United States Patent
Fan et al.

(10) Patent No.: US 8,557,771 B2
(45) Date of Patent: Oct. 15, 2013

(54) HOMODIMER OF INSULINOTROPIC PEPTIDE ANALOGUES AND METHOD FOR PREPARATION THEREOF AND USE THEREOF

(75) Inventors: Kai Fan, Jiulongpo Chongqing (CN); Zhiquan Zhao, Jiulongpo Chongqing (CN); Yong Chen, Jiulongpo Chongqing (CN); Chun Zhang, Jiulongpo Chongqing (CN); Lin Wang, Jiulongpo Chongqing (CN)

(73) Assignee: Chongqing Fagen Biomedical Inc., Jiulongpo Chongqing (CN)

( * ) Notice: Subject to any disclaimer, the term of this patent is extended or adjusted under 35 U.S.C. 154(b) by 0 days.

(21) Appl. No.: 13/391,097

(22) PCT Filed: Mar. 15, 2010

(86) PCT No.: PCT/CN2010/071036
§ 371 (c)(1),
(2), (4) Date: Feb. 29, 2012

(87) PCT Pub. No.: WO2011/020320
PCT Pub. Date: Feb. 24, 2011

(65) Prior Publication Data
US 2012/0277154 A1 Nov. 1, 2012

(30) Foreign Application Priority Data

Aug. 20, 2009 (CN) .......................... 2009 1 0104650

(51) Int. Cl.
C07K 19/00 (2006.01)
A61P 3/00 (2006.01)
A61K 38/26 (2006.01)
C07K 14/43 (2006.01)

(52) U.S. Cl.
CPC ..................................... *C07K 14/43* (2013.01)
USPC ......................................... 514/11.7; 530/308

(58) Field of Classification Search
None
See application file for complete search history.

(56) References Cited

FOREIGN PATENT DOCUMENTS

| WO | 2006/124529 | 11/2006 | | |
|----|-------------|---------|---|---|
| WO | 2007/039140 | 4/2007  | | |
| WO | 2008/101017 | 8/2008  | | |
| WO | WO2008101017 | * | 8/2008 | ............. C07K 14/43 |

OTHER PUBLICATIONS

Chalker et al. "Chemical Modification of Proteins at Cysteine: Opportunities in Chemistry and Biology" (2009) Chem. Asian. J. 4:630-640.*
Kieffer et al "The Glucagon-Like Peptides" (1999) Endocrine Reviews 20(6): 876-913.*
Exendin-4 Amino Acid Sequence, CAS No. 141758-74-9, Sigma Aldrich MSDS (accessed Feb. 10, 2013).*
Doyle et al "In vivo biological activity of exendin (1-30)." Endocrine (Jun. 2005) 27(1): 1-9.*
Simonsen et al. "The C-terminal extention of exendin-4 provides additional metabolic stability when added to GLP-1 while there is minimal effect of truncating exendin-4 in anaesthetized pigs." (2013) 181:17-21.*
International Search Report of International Application No. PCT/CN2010/071036, mailed Jun. 17, 2010.

* cited by examiner

Primary Examiner — Jean C. Witz
Assistant Examiner — Mindy Newman
(74) Attorney, Agent, or Firm — Ping Wang; Andrews Kurth LLP

(57) ABSTRACT

Provided is a homodimer of insulinotropic peptide analogues and method for preparation thereof and use thereof, wherein the insulinotropic peptide analogue comprises GLP-1 and Exendin-4. The homodimer of insulinotropic peptide analogues of the invention is made by conjugating two identical insulinotropic peptide analogue molecules at the C-terminal Cys residues via disulfide bond or PEG molecule. The homodimer of insulinotropic peptide analogues of the invention has superior stability and biological activity in vivo, and prolonged half-life in the circulation, and can be used for the preparation of hypoglycemic drugs.

7 Claims, 5 Drawing Sheets

SEQ ID NO:1   His Gly Glu Gly Thr Phe Thr Ser Asp Val Ser Ser Tyr Leu Glu Gly
SEQ ID NO:2   His Gly Glu Gly Thr Phe Thr Ser Asp Leu Ser Lys Gln Met Glu Glu

SEQ ID NO:1  Gln Ala Ala Lys Glu Phe Ile Ala Trp Leu Val Lys Xaa Cys-OH (NH₂)
SEQ ID NO:2  Glu Ala Val Arg Leu Phe Ile Glu Trp Leu Lys Asn Xaa Cys-OH (NH₂)

Fig.1

SEQ ID NO:3   His Gly Glu Gly Thr Phe Thr Ser Asp Leu Ser Lys Gln Met Glu Glu
SEQ ID NO:4   His Gly Glu Gly Thr Phe Thr Ser Asp Val Ser Ser Tyr Leu Glu Gly

SEQ ID NO:3   Glu Ala Val Arg Leu Phe Ile Glu Trp Leu Lys Asn Gly Gly Ser Gly
SEQ ID NO:4   Gln Ala Ala Lys Glu Phe Ile Ala Trp Leu Val Lys Gly Gly Gly Gly

SEQ ID NO:3   Gly Ser Cys
SEQ ID NO:4   Gly Ser Cys

Fig.2

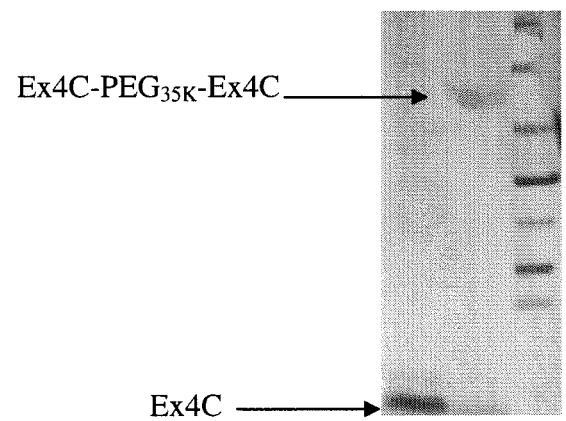
A
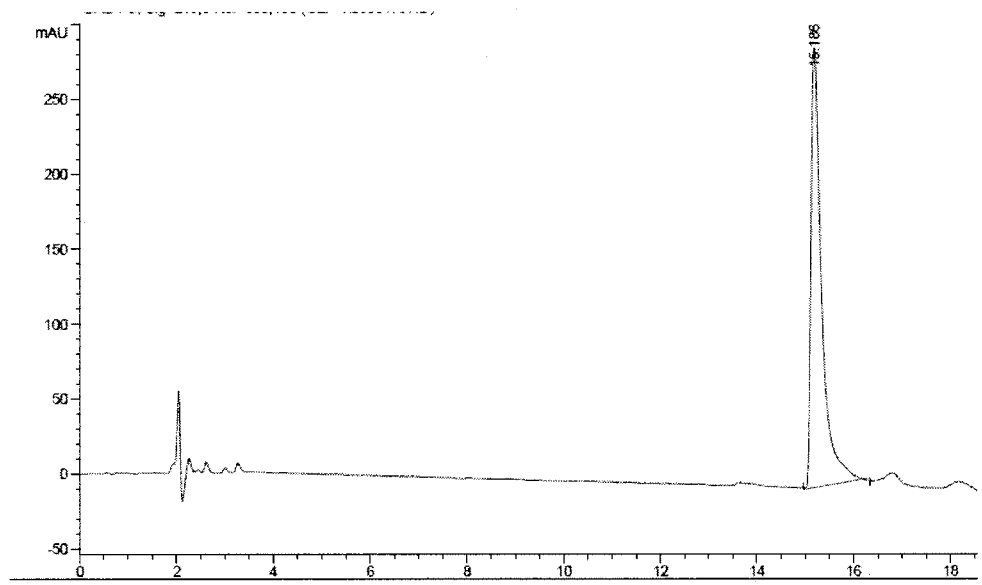
B
Fig.3

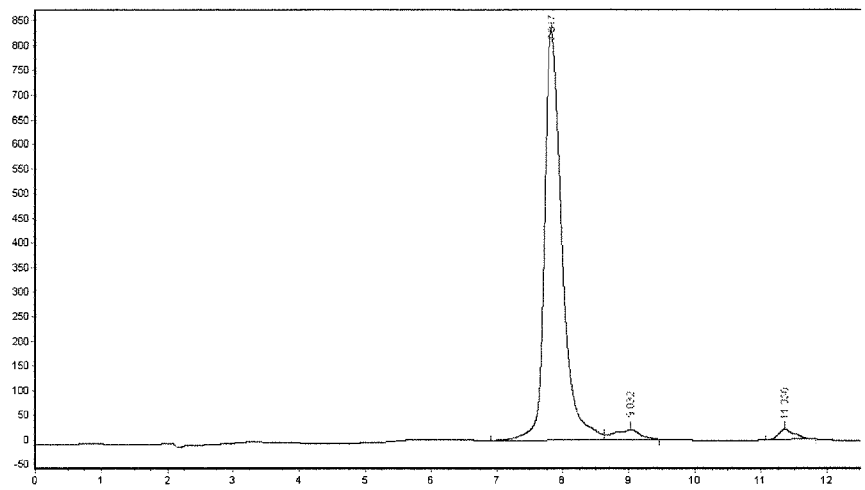
A
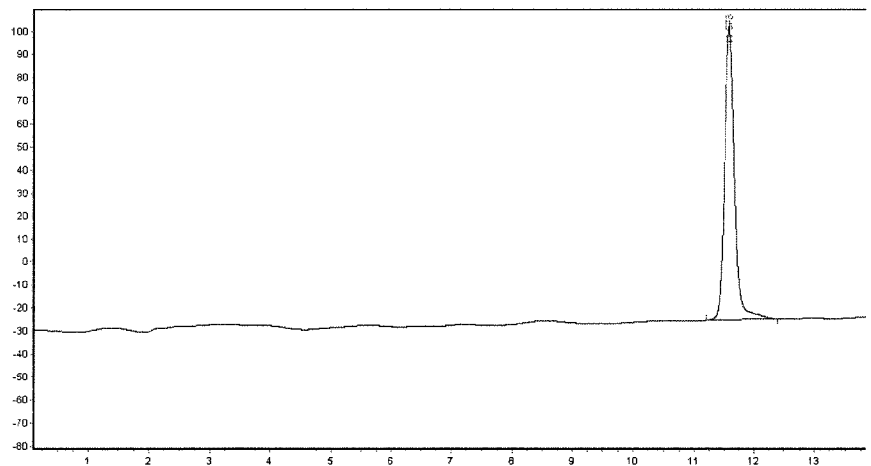
B
Fig.4

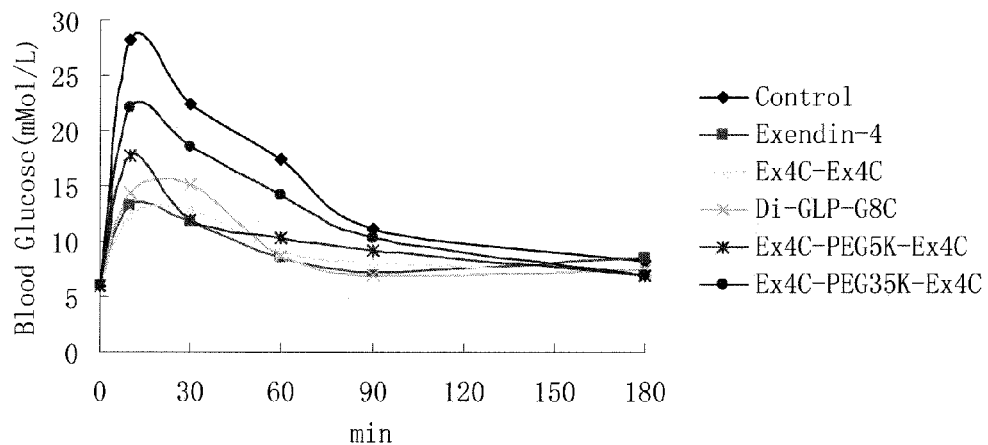
A
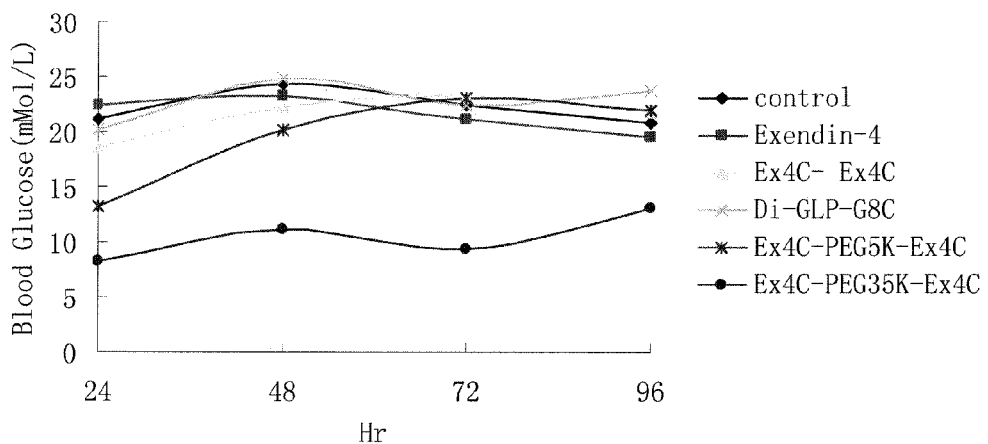
B
Fig.5

HOMODIMER OF INSULINOTROPIC PEPTIDE ANALOGUES AND METHOD FOR PREPARATION THEREOF AND USE THEREOF

FIELD

The invention relates to biotechnology and pharmaceutical, especially to a homodimer of insulinotropic peptide analogues, and preparation method thereof and use thereof.

BACKGROUND

Glucagon-like peptide (GLP) is an intestinal hormone secreted in human bodies, which is produced from the enzymatic lysis of proglucagon by intestinal protein hydrolase, wherein two kinds of glucagon-like peptides are generated, namely, GLP-1 and GLP-2. GLP-1 has two active forms, the GLP-1 (7-37) and the GLP-1 (7-36) with amidation, which possess with the same insulinotropic activity in vivo and are called Incretin or Insulinotropic peptide (Negar Sadrzadeh et al., Pharmaceutical Sciences, Vol. 96, 1925-1954 (2007)).

Exendin-4 is a polypeptide of 39 amino acids found in *Heloderma horridurn* venom, and shares similarities with many members of the GLP family, e.g., 53% homology with GLP-1 (7-36) (Eng J et al., J Biol Chem, 1992, 267: 7402-7405). As a strong GLP-1R agonist, Exendin-4 has been proved to be insulinotropic both in vivo and in vitro, and therefore can also be taken as an insulinotropic peptide. Amino acid sequences of GLP-1 (7-36) and Exendin-4 are as followings:

```
GLP-1 (7-36):
His Ala Glu Gly Thr Phe Thr Ser Asp Val Ser Ser

Tyr Leu Glu Gly Gln Ala Ala Lys Glu Phe Ile Ala

Trp Leu Val Lys Gly Arg

Exendin-4:
His Gly Glu Gly Thr Phe Thr Ser Asp Leu Ser Lys

Gln Met Glu Glu Glu Ala Val Arg Leu Phe Ile Glu

Trp Leu Lys Asn Gly Gly Pro Ser Ser Gly Ala Pro

Pro Pro Ser
```

With Gly2 at the N-terminal, which is different from the Ala in GLP-1, Exendin-4 can effectively resist to the degradation of DPP IV. Furthermore, Exendin-4 comprises 9 amino acids (PSSGAPPPS) at the C-terminal that do not exist in GLP-1, making it unlikely to be digested by endonuclease, and is enhanced with the affinity to bind to GLP-1 receptors. Therefore, the blood sugar regulation ability of Exendin-4 is thousands of times more than that of GLP-1 in vivo. There are many analogues of Exendin-4, e.g. ZP10 a GLP-1 analogue with 5-lysine (KKKKK) added at the C-terminal of Exendin-4 (Petersen J S, Diabetologia, 2002, 45: A147); analogues with Lys20 substituted by Arg or His, Trp25 by Phe, and Met14 by Leu or Ile; as well as those with deletions at the C-terminal of Exendin-4, namely Exendin-4 (1-28) or Exendin-4 (1-30) and amidation forms thereof (Vilsbøll T, Diabetes Care, 2007, 30: 1608-1610).

Analogues of GLP-1 (7-36) and Exendin-4 are thus generated by the above modifications, comprising substitutions of one or more amino acids, or deletion or addition of the amino acid at the C-terminal.

GLP-1 (7-36) and Exendin-4, which have half-lives of only about 2 min and 2 hours in vivo, respectively, are reported in many patent publications and literatures to be fused to human blood albumin, the Fc fragment of human IgG or transferrin, to prolong the half-life (e.g., GLP-1-HSA, GLP-1-Fc, GLP-1-Transferrin, Exendin4-HAS, Exendin4-Fc, etc.; see U.S. Pat. No. 7,271,149; US2007/0036806A1; US 2007/0060512A1; US2006/0293232A1; and US2007/0161087A1). The above fusion proteins are mainly expressed and prepared using recombinant technology in host cells such as *E. coli*, yeast and mammalian cells (Xiaopu Yin et al., Protein Expression and Purification, 41 (2005), 259-265; Jin Zhou et al., Biotechnol Lett (2008) 30: 651-656; Fehmann H C et al., Peptides, 1994, 15(3): 453-456).

GLP-1 or Exendin-4 are reported to be modified by PEG in other patent publications and literatures, wherein they are conjugated mainly at the amino group of lysine, or COOH at the C-terminal (U.S. Pat. No. 6,284,727, U.S. Ser. No. 9/561,226), to prolong the half-life in vivo.

GLP-1 is also modified chemically at the aliphatic chain (e.g., Liraglutide) or at specific amino acids (Lys34) (e.g., CJC-1131) to be bound to albumin, so that it can be administrated once a day (with a half-life of 11-15 hours) (Kim, J G, Diabetes, 2003 March; 52(3): 751-759).

Besides of chemical solid-phase synthesis, GLP-1 and Exendin-4 are also reported to be expressed using recombinant DNA methods in literatures and patents, such as recombinant expression in *E. coli* (Xiaopu Yin et al., Protein Expression and Purification, 41 (2005)259-265); as well as in *Pichia pastoris* (Jin Zhou et al., Biotechnol Lett (2008) 30: 651-656). Furthermore, Exendin-4 is reported to be expressed in series as a dimer (Lina Yin et al., Protein & Peptide Letters, 2006, 13, 823-827).

GLP-1 or Exendin-4 mainly possesses with the following biological functions, including: (1) acting with pancreas islet β-cells to stimulate the synthesis and release of insulin; (2) inhibiting the release of glucagon and promoting the synthesis of glycogen; (3) increasing insulin sensitivity and sugar tolerance; (4) improving the proliferation and activity of pancreas islet (3-cell to reduce cell apoptosis; (5) reducing the rate of stomach evacuation; and (6) inhibiting appetite and energy uptake. Therefore, Exendin-4 (Trade name as Byetta) and Liraglutide have been granted to be polypeptide drugs for the treatment of diabete II, and relevant studies have been focused in the area.

BRIEF DESCRIPTION OF THE DRAWINGS

The invention is described in details hereto, and can be further illustrated with reference to the following examples and drawings.

FIG. 1: Alignment of amino acid sequences of insulinotropic peptide analogues derived from GLP-1 (Gly[8] 7-34) (SEQ ID NO: 1) and from Exendin-4 (1-28) (SEQ ID NO: 2).

FIG. 2: Alignment of amino acid sequence of Ex4C (SEQ ID NO: 3) and GLP-G8C (SEQ ID NO: 4).

FIG. 3: SDS-PAGE (a) and RP-HPLC (b) of Ex4C-PEG35K-Ex4C.

FIG. 4: RP-HPLC of Ex4C and Ex4C-Ex4C, wherein Fig. A shows the Ex4C monomer and Fig. B shows the Ex4C-Ex4C homodimer.

FIG. 5: Blood sugar regulation of Ex4C-PEG5k-Ex4C, Ex4C-PEG35k-ExC, Ex4C-Ex4C and Exendin-4 (WT) in mice in vivo.

DETAILED DESCRIPTION

Figure 6:
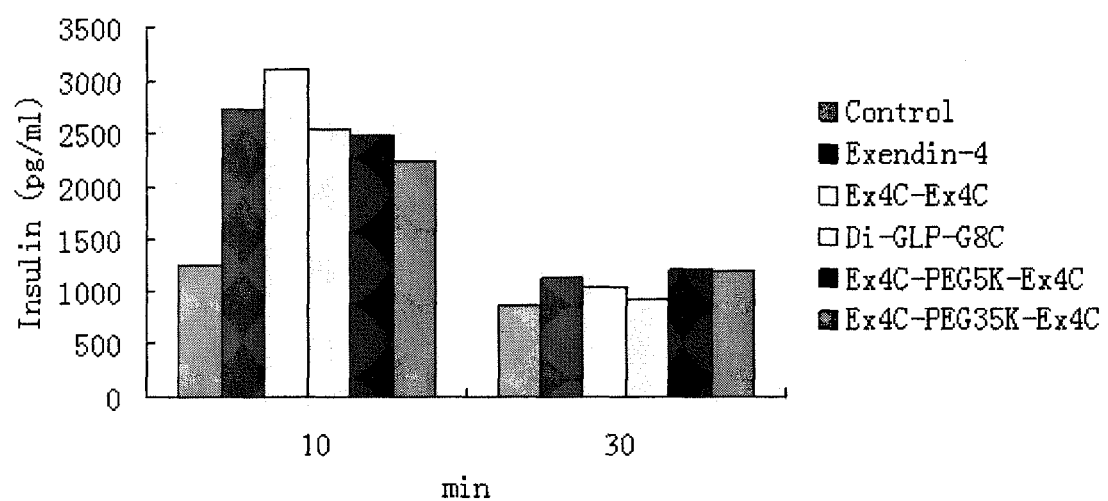
FIG. 6: Insulinotropic effects of Ex4C-PEG$_{5k}$-Ex4C, Ex4C-PEG$_{35k}$-Ex4C, Ex4C-Ex4C and Exendin-4 (WT) in mice in vivo.

Provided is a homodimer of insulinotropic peptide analogues derived from GLP-1 or Exendin-4, and method for preparation thereof, wherein the insulinotropic peptide analogue possesses with superior stability and biological activity in vivo and prolonged circulating half-life, and can be used for the preparation of hypoglycemic drugs.

Also provided is a homodimer of insulinotropic peptide analogues, which is made by conjugating two identical insulinotropic peptide analogues at the C-terminal.

Said insulinotropic peptide analogues are GLP-1 derivatives with an amino acid sequence of SEQ ID NO: 1: His Gly Glu Gly Thr Phe Thr Ser Asp Val Ser Ser Tyr Leu Glu Gly Gln Ala Ala Lys Glu Phe Ile Ala Trp Leu Val Lys Xaa Cys-N, wherein N is —OH or —NH$_2$, and Xaa is:
- A: (GlyGlySer)n, or (GlyGlyPro)n, wherein n is an integer between 1-5;
- B: (Gly)n, or (Gly)n Ser, wherein n is an integer between 4-20; or
- C: any combination of A or B.

Or, said insulinotropic peptide analogues are Exendin-4 derivatives with amino acid sequence of SEQ ID NO: 2: His Gly Glu Gly Thr Phe Thr Ser Asp Leu Ser Lys Gln Met Glu Glu Glu Ala Val Arg Leu Phe Ile Glu Trp Leu Lys Asn Xaa Cys-N, wherein N is —OH or —NH$_2$, and Xaa is:
- A: (GlyGlySer)n, or (GlyGlyPro)n, wherein n is an integer between 1-5;
- B: (Gly)n, or (Gly)n Ser, wherein n is an integer between 4-20; or
- C: any combination of A or B.

The Xaa sequence can be designed by those skilled in the art without affecting the activity.

The insulinotropic peptide analogues comprising amino acid sequences of SEQ ID NO: 1 and SEQ ID NO: 2 possess with a C-terminal amino acid residue of cysteine or the amidation form thereof.

Said insulinotropic peptide analogues can also be peptides obtained by substitution, deletion or addition of one or several amino acid residues of SEQ ID NO: 1 or 2, and share more than 50% of homology with the original SEQ ID NO: 1 or 2, while remaining activities of promoting insulin secretion and regulating blood sugar.

The two identical insulinotropic peptide analogues are conjugated at the C-terminal by PEG molecule.

PEG molecules used in the homodimer of insulinotropic peptide analogues of the invention can be small or large; with molecular weights between 500 D and 40 KD. The half-life of the homodimer of insulinotropic peptide analogues can be significantly prolonged in vivo using PEG molecules with the molecular weight of over 5000. Preferred PEG molecular weight is between 500 D and 40 KD.

Also provided is a method for preparing the homodimer of insulinotropic peptide analogues, wherein the two identical insulinotropic peptide analogues are conjugated at the C-terminal Cys residues via disulfide bond oxidated from free sulfhydryl (or sulpho) thereon.

Also provided is a method for preparing the homodimer of insulinotropic peptide analogues, wherein double-activated PEG molecule is used as a linker that is conjugated to the free sulfhydryls at the C-terminal of the two identical insulinotropic peptide analogues to generate a homodimer with structure as followings:

GLP-1-Cys-PEG-Cys-GLP-1 or Exendin4-Cys-PEG-Cys-Exendin4.

The double-activated PEG molecule is a double-activated maleimide-PEG, with molecular structure of MAL-PEG-MAL; or double-activated sulfhydryl-PEG, with molecular structure of SH-PEG-SH; or double-activated ortho-pyridyldisulfide-PEG, with molecular structure of OPSS-PEG-OPSS; or double-activated iodo acetamide-PEG, with molecular structure of IA-PEG-IA; or double-activated vinyl-sulfone-PEG, with molecular structure of VS-PEG-VS.

PEG molecules used in the homodimer of insulinotropic peptide analogues of the invention can be small or large, with the molecular weight between 500 D and 40 KD. The half-life of the homodimer of insulinotropic peptide analogues can be significantly prolonged in vivo using PEG molecules with the molecular weight of over 5000. Preferred PEG molecular weight is between 500 D and 40 KD.

Another aim of the invention is to provide method for preparing insulinotropic peptide analogues by chemical solid-phase synthesis or recombinant DNA technology. By recombinant DNA technology, cDNA gene fragments encoding insulinotropic peptide analogues are inserted into an expression vector, which is then transformed into a host cell, and the recombinant peptide is expressed and purified after the fermentation or culture of cells.

Another aim of the invention is to provide methods for separation and purification of the homodimer of insulinotropic peptide analogues, including routine ion-exchange chromatography, affinity chromatography, hydrophobic interaction chromatography, reverse phase chromatography, as well as ultrafiltration, etc.

Also provided is a drug for the treatment of metabolism syndromes related to diabetes or hyperglycemia, which comprises the homodimer of insulinotropic peptide analogues. Furthermore, the drug may comprise pharmaceutically acceptable vectors or excipients or diluents.

The "homodimer" of the invention refers to a dimer made by conjugating two identical insulinotropic peptide analogues at the C-terminal.

The "PEG conjugation" of the invention refers to the PEG-ylated homodimer derived from the conjugation of two identical insulinotropic peptide analogues linked at the C-terminal by PEG molecules with different molecular weights.

The "host cell" of the invention refers to E. coli or yeast.

The "expression vector" of the invention refers to E. coli expression vectors comprising promotors such as T7, Tac, Trp or Lac; or yeast expression vectors comprising α-secretion factor and promoters AOX or GAP.

The following examples are listed only for illustration, and meant no limitations to the invention.

Embodiments

EXAMPLE 1

Solid-phase synthesis of Ex4C and GLP-G8C

The amino acid sequence of Ex4C and GLP-G8C were as followings:

```
Ex4C (SEQ ID NO: 3):
His Gly Glu Gly Thr Phe Thr Ser Asp Leu Ser Lys

Gln Met Glu Glu Glu Ala Val Arg Leu Phe Ile Glu

Trp Leu Lys Asn Gly Gly Ser Gly Gly Ser Cys
```

-continued

GLP-G8C (SEQ ID NO: 4):
His Gly Glu Gly Thr Phe Thr Ser Asp Val Ser Ser

Tyr Leu Glu Gly Gln Ala Ala Lys Glu Phe Ile Ala

Trp Leu Val Lys Gly Gly Gly Gly Ser Cys

With peptides having carboxyl at the C-terminal, Wang resin was used for the solid-phase synthesis and products with protecting groups at side chains were cleaved from the resin, leaving a carboxyl group at the C-terminal of Ex4C or GLP-G8C. In addition, with peptides having amidation form at the C-terminal, Fmoc-PAL-PEG-PS resin was used for solid-phase synthesis, and products with protecting groups at side chains was cleaved from the resin, leaving amidation form at the C-terminal of Ex4C or GLP-G8C.

The above solid-phase synthesis was carried out in a peptidesynthesizer (ABI Corp.), wherein the C-terminal Cys was connected to the resin firstly and then other amino acids one by one from C- to N-terminal. After the synthesis was accomplished, the peptide was de-protected and cleaved from the resin, and Ex4C or GLP-G8C was purified with reverse HPLC (Waters Corp., C18 preparative column) under conditions of: 0.5% (V/V) of acetic acid solution as Solution A, 80% acetonitrile and 0.5% (V/V) of acetic acid solution as Solution B, with gradient elution with 0-100% of Solution B. The target peptide was collected and lyophilized to dry powder. The molecular weight was assayed by mass spectrography, with 4019.39 for Ex4C-$NH_2$ and 3521.87 for GLP-G8C-$NH_2$, which was identical with theoretical values.

EXAMPLE 2

Recombinant Expression of Ex4C in *E. coli*

A cDNA sequence based on the Ex4C in Example 1 (SEQ ID NO: 3) was synthesized according to the code preference of *E. coli* by TaKaRa Biotechnology (DaLian) co., ltd.

```
CDNA sequence of Ex4C
                                                              (SEQ ID NO: 5)
ggtaccgacg acgacgacaa gcatggcgaa ggcacctta ccagcgatct gagcaaacag    60
atggaagaag aagcggtgcg tctgtttatt gaatggctga aaaatggcgg cagcggcggc   120
agctgctagg aattc                                                    135
```

The synthesized cDNA fragment (in pMD-18 plasmid) was digested with KpnI and EcoRI, to be inserted into pET32a plasmid (NOVAGEN Corp.) by T4 ligase. The product was transformed into *E. coli*. DH5α. Recombinant plasmid comprising Ex4C gene was selected and named as pET32a-Ex4C, which was then transformed into BL21 (DE3-plys) by $CaCl_2$ transformation method. TRX-EK-Ex4C fusion protein was expressed after being induced with 0.5 mmol/L of IPTG. After being purified with Ni-Sepharose chromatography, the fusion protein was deprived with thioredoxin (TRX) by enterokinase, and the recombinant Ex4C was purified with C18 reverse-phase column and lyophilized to dry powder.

EXAMPLE 3

Preparation of the Ex4C-Ex4C Homodimer

The Ex4C($NH_2$) of Example 1 with more than 98% purity was dissolved in a 50 mmol/L Tris-Cl (pH8.5) buffer with a final concentration of 1.0-2.0 mg/ml. After being reacted overnight in 4° C., or for 4-6 hours at room temperature, 90% of Ex4C became homodimers, namely Ex4C-Ex4C, which was determined by RP-HPLC. The reaction was terminated by the addition of 1% of TFA, and the Ex4C-Ex4C homodimer was purified with C18 column and lyophilized to dry powder. The molecular weight was assayed by mass spectrography, and the result showed identical with the theoretical value, i.e., 8036.68.

EXAMPLE 4

Preparation of the GLP-G8C Homodimer

The GLP-G8C of Example 1 with more than 98% purity was dissolved in a 50 mmol/L Tris-Cl (pH8.5) buffer with a final concentration of 1.0-2.0 mg/ml. After being reacted overnight in 4° C. or for 4-6 hours at room temperature, 90% of GLP-G8C became homodimers, namely Di-GLP-G8C, which was assayed by RP-HPLC. The reaction was terminated by the addition of 1% of TFA, and the Di-GLP-G8C homodimer was purified with C18 column and lyophilized to dry powder.

EXAMPLE 5

Preparation of the Ex4C-PEG5K-Ex4C Dimer

SH-PEG5K-SH (from Jiankai Corp., Beijing) was dissolved by 20.0 mg/ml in a 100 mmol/L sodium phosphate buffer (pH6.5), and Ex4C was added slowly with agitation at room temperature or 4° C., till the molar ratio of PEG5K:Ex4C is 1: 2-4. After being reacted for 4-12 hours, the PEG-coupled dimmer was determined to be more than 85% by RP-HPLC with an evaporative light scattering detector (ELSD). The reaction was terminated by the addition of 1% of TFA, and unmodified Ex4C and PEG-modified single-stranded PEG5K-Ex4C were removed with C18 column. The purified Ex4C-PEG5K-Ex4C dimmer was lyophilized to dry powder.

EXAMPLE 6

Preparation of the Ex4C-PEG35K-Ex4C Dimer

MAL-PEG35K-MAL (from Jiankai Corp., Beijing) was dissolved by 20.0 mg/ml in a 100 mmol/L sodium phosphate buffer (pH6.5), and Ex4C was added slowly with agitation at room temperature or 4° C., till the molar ratio of PEG35K:Ex4C is 1: 2-4. After being reacted for 4-12 hours, the PEG-coupled dimmer was determined to be more than 85% by RP-HPLC with an evaporative light scattering detector (ELSD). The reaction was terminated by the addition of 1% of TFA, and unmodified Ex4C and PEG-modified single-stranded PEG35K-Ex4C were removed with C18 column. The purified Ex4C-PEG35K-Ex4C dimmer was lyophilized to dry powder.

EXAMPLE 7

Effect of Four Dimmers of Insulinotropic Peptide Analogues on Blood Sugar Regulation in Mice In Vivo Balb/c mice of 20-25 grams (from Laboratory Animal Center, Chongqing Medical University) were divided into 6 groups, 10 mice for each, comprising: the control (normal saline), Exendin-4 (synthesized by Xunti biotechnology Corp., Chengdu), Ex4C-Ex4C, Di-GLP-G8C, Ex4C-PEG5K-Ex4C and Ex4C-PEG35K-Ex4C. After fasting overnight, mice were intraperitoneally injected respectively with 100 µl of different drugs that were dissolved to 10 nmol/L in a 10 mmol/L sodium phosphate buffer (pH6.5), and meanwhile injected with 200 µl of glucose solution (40%). Blood was sampled at 30, 60, 120, and 180 min after drug administration and blood sugar was assayed (Blood sugar meter, LifeScan, Inc.). Then, 200 µl of glucose solution (40%) was intraperitoneally injected again at 24 hours, 48 hours, 72 hours and 96 hours after drug administration, respectively. Blood was sampled at 30 and 60 min after glucose administration and blood sugar was assayed (Blood sugar meter, LifeScan, Inc.).

Results showed that (FIG. 5), the blood sugar level was well-regulated 3 hours after the administration of homodimers Ex4C-Ex4C and Di-GLP-G8C, and the effect lasted for no more than 24 hours. However, the blood sugar regulation effect of homodimers Ex4C-PEG5K-Ex4C and Ex4C-PEG35K-Ex4C maintained until 24 hours and 96 hours, respectively.

EXAMPLE 8

Insulinotropic Effect of Four Dimmers of Insulinotropic Peptide Analogues in Mice In Vivo Balb/c mice of 20-25 grams (from Laboratory Animal Center, Chongqing Medical University, clean grade) were divided into 6 groups, 10 mice for each, comprising: the control (normal saline), Exendin-4, Ex4C-Ex4C, Di-GLP-G8C, Ex4C-PEG5K-Ex4C and Ex4C-PEG35K-Ex4C. After fasting overnight, mice were intraperitoneally injected respectively with 100 µl of different drugs that were dissolved to 10 nmol/L in a 10 mmol/L sodium phosphate buffer (pH6.5).

Assays: Animals in each group were intraperitoneally injected with 100 µl of glucose solution (40%) and meanwhile with different drugs of the same volume. 20 µl of blood was sampled (from eye sockets) at 10 and 30 min after drug administration to a centrifuge tube containing 20 µl of 1% EDTA. After centrifugation, the insulin level was detected in serum using insulin assay kits (Northen Isotope Corp.).

Results showed that (FIG. 6), the insulin secretion was significantly enhanced at 10 min after the administration of the four dimers of insulinotropic peptide analogues in mice in vivo.

The invention claimed is:

1. A homodimer of insulinotropic peptide analogues, prepared by:
   conjugating two identical insulinotropic peptide analogues at the C-terminal,
   wherein the insulinotropic peptide analogues are Exendin-4 derivatives with the amino acid sequence of SEQ ID NO:2: His Gly Glu Gly Thr Phe Thr Ser Asp Leu Ser Lys Gln Met Glu Glu Glu Ala Val Arg Leu Phe Ile Glu Trp Leu Lys Asn Xaa Cys-N,
   wherein N is —OH or —NH$_2$, and
   wherein Xaa is:
   A: (GlyGlySer)n, or (GlyGlyPro)n, wherein n is an integer between 1-5;
   B: (Gly) n, or (Gly) n Ser, wherein n is an integer between 4-20; or
   C: any combination of A or B.

2. The homodimer of insulinotropic peptide analogues according to claim 1, wherein the insulinotropic peptide analogue has a C-terminal amino acid residue of cysteine or the amidation form thereof.

3. The homodimer of insulinotropic peptide analogues according to claim 1, wherein two identical insulinotropic peptide analogues are conjugated at the C-terminal by a PEG molecule, generating a structure of Exendin4-Cys-PEG-Cys-Exendin4.

4. The homodimer of insulinotropic peptide analogues according to claim 3, wherein the molecular weight of PEG is between 10 KD and 40 KD.

5. A method for preparing a homodimer of insulinotropic peptide analogues, comprising:
   conjugating two identical insulinotropic peptide analogues at the C-terminal Cys residue via disulfide bond oxidated from free sulfhydryl thereon,
   wherein said two identical insulinotropic peptide analogues are Exendin-4 derivatives with the amino acid sequence of SEQ ID NO:2: His Gly Glu Gly Thr Phe Thr Ser Asp Leu Ser Lys Gln Met Glu Glu Glu Ala Val Arg Leu Phe Ile Glu Trp Leu Lys Asn Xaa Cys-N,
   wherein N is —OH or —NH$_2$, and
   wherein Xaa is:
   A: (GlyGlySer)n, or (GlyGlyPro)n, wherein n is an integer between 1-5;
   B: (Gly) n, or (Gly) n Ser, wherein n is an integer between 4-20; or
   C: any combination of A or B.

6. A drug for the treatment of metabolism syndromes related to diabetes or hyperglycemia, comprising a homodimer of insulinotropic peptide analogues prepared by conjugating two identical insulinotropic peptide analogues at their C-terminal Cys residues,
   wherein the insulinotropic peptide analogues are Exendin-4 derivatives with the amino acid sequence of SEQ ID NO:2: His Gly Glu Gly Thr Phe Thr Ser Asp Leu Ser Lys Gln Met Glu Glu Glu Ala Val Arg Leu Phe Ile Glu Trp Leu Lys Asn Xaa Cys-N,
   wherein N is —OH or —NH$_2$, and
   wherein Xaa is:
   A: (GlyGlySer)n, or (GlyGlyPro)n, wherein n is an integer between 1-5;
   B: (Gly) n, or (Gly) n Ser, wherein n is an integer between 4-20; or
   C: any combination of A or B.

7. The drug according to claim 6, further comprising a pharmaceutically acceptable vector or an excipient or a diluent.

* * * * *

```
                        SEQUENCE LISTING

<160> NUMBER OF SEQ ID NOS: 7

<210> SEQ ID NO 1
<211> LENGTH: 30
<212> TYPE: PRT
<213> ORGANISM: Artificial Sequence
<220> FEATURE:
<223> OTHER INFORMATION: Insulinotropic peptide analogue of GLP-1
<220> FEATURE:
<221> NAME/KEY: Xaa
<222> LOCATION: (29)..(29)
<223> OTHER INFORMATION: Xaa is A, B or C, where: A can be (GlyGlySer)n
      or (GlyGlyPro)n and where n is an integer between 1-5; B can be
      (Gly)n or (Gly)n(Ser), where n is an integer between 4-20; C is
      any combination of A or B

<400> SEQUENCE: 1

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Xaa Cys
            20                  25                  30

<210> SEQ ID NO 2
<211> LENGTH: 30
<212> TYPE: PRT
<213> ORGANISM: Artificial Sequence
<220> FEATURE:
<223> OTHER INFORMATION: Insulinotropic peptide analogue of Extendin-4
<220> FEATURE:
<221> NAME/KEY: Xaa
<222> LOCATION: (29)..(29)
<223> OTHER INFORMATION: Xaa is A, B or C, where: A can be (GlyGlySer)n
      or (GlyGlyPro)n and where n is an integer between 1-5; B can be
      (Gly)n or (Gly)n(Ser), where n is an integer between 4-20; C is
      any combination of A or B

<400> SEQUENCE: 2
```

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Xaa Cys
            20                  25                  30

<210> SEQ ID NO 3
<211> LENGTH: 35
<212> TYPE: PRT
<213> ORGANISM: Artificial Sequence
<220> FEATURE:
<223> OTHER INFORMATION: Ex4C peptide sequence

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Ser Gly
            20                  25                  30

Gly Ser Cys
        35

<210> SEQ ID NO 4
<211> LENGTH: 35
<212> TYPE: PRT
<213> ORGANISM: Artificial Sequence
<220> FEATURE:
<223> OTHER INFORMATION: GLP-G8C peptide sequence

<400> SEQUENCE: 4

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Gly Gly Gly
            20                  25                  30

Gly Ser Cys
        35

<210> SEQ ID NO 5
<211> LENGTH: 135
<212> TYPE: DNA
<213> ORGANISM: Artificial Sequence
<220> FEATURE:
<223> OTHER INFORMATION: cDNA sequence of Ex4C
<220> FEATURE:
<221> NAME/KEY: Other
<222> LOCATION: (1)..(135)
<223> OTHER INFORMATION: Synthetic cDNA for Ex4C

<400> SEQUENCE: 5
ggtaccgacg acgacgacaa gcatggcgaa ggcaccttta ccagcgatct gagcaaacag      60
atggaagaag aagcggtgcg tctgtttatt gaatggctga aaaatggcgg cagcggcggc     120
agctgctagg aattc                                                      135

<210> SEQ ID NO 6
<211> LENGTH: 9
<212> TYPE: PRT
<213> ORGANISM: Artificial Sequence
<220> FEATURE:
<223> OTHER INFORMATION: C-terminal sequence in Extendin-4

<400> SEQUENCE: 6

Pro Ser Ser Gly Ala Pro Pro Pro Ser
1               5

<210> SEQ ID NO 7
<211> LENGTH: 5

```
<212> TYPE: PRT
<213> ORGANISM: Artificial Sequence
<220> FEATURE:
<223> OTHER INFORMATION: C-terminal extension in ZP10, a GLP-1 analogue

<400> SEQUENCE: 7

Lys Lys Lys Lys Lys
1               5
```